(12) United States Patent
Loy, Jr.

(10) Patent No.: US 7,316,777 B2
(45) Date of Patent: Jan. 8, 2008

(54) COMPRESSION FITTING NUT WITH INTERLOCKED FERRULE

(75) Inventor: H. Max Loy, Jr., Houston, TX (US)

(73) Assignee: Valco Instruments Co., Inc., Houston, TX (US)

( * ) Notice: Subject to any disclaimer, the term of this patent is extended or adjusted under 35 U.S.C. 154(b) by 228 days.

(21) Appl. No.: 11/333,944

(22) Filed: Jan. 18, 2006

(65) Prior Publication Data
US 2006/0169628 A1   Aug. 3, 2006

Related U.S. Application Data

(60) Provisional application No. 60/648,135, filed on Jan. 28, 2005.

(51) Int. Cl.
*B01D 15/08* (2006.01)

(52) U.S. Cl. .................. 210/198.2; 210/656; 285/343

(58) Field of Classification Search .............. 210/656, 210/659, 198.2, 232, 450; 95/82; 96/101; 285/343
See application file for complete search history.

(56) References Cited

U.S. PATENT DOCUMENTS

| | | | |
|---|---|---|---|
| 3,904,527 A * | 9/1975 | Wilhelmson et al. .... | 210/198.2 |
| 4,506,987 A | 3/1985 | Daughton et al. | |
| RE31,974 E * | 8/1985 | Brownlee ................ | 210/198.2 |
| 4,792,396 A * | 12/1988 | Gundelfinger .......... | 210/198.2 |
| 5,169,120 A | 12/1992 | Guthrie, Jr. et al. | |
| 5,582,723 A * | 12/1996 | Boone et al. ........... | 210/198.2 |
| 5,730,943 A * | 3/1998 | Ford et al. .............. | 422/101 |
| 5,938,919 A * | 8/1999 | Najafabadi ............. | 210/198.2 |
| 6,056,331 A | 5/2000 | Benett et al. | |
| 6,162,362 A * | 12/2000 | Ma et al. ................. | 210/656 |
| 6,494,500 B1 | 12/2002 | Todosiev et al. | |
| 6,851,729 B2 * | 2/2005 | Gibson ..................... | 285/341 |
| 2004/0238447 A1 * | 12/2004 | Cheong ................... | 210/656 |
| 2005/0077218 A1 * | 4/2005 | Nyudo et al. ........... | 210/94 |

* cited by examiner

*Primary Examiner*—Ernest G. Therkorn
(74) *Attorney, Agent, or Firm*—James E. Hudson, III; Crain, Caton & James, P.C.

(57) ABSTRACT

The invention pertains to a nut and ferrule assembly for use in joining tubing to a fitting. The ferrule has a male member which interlocks with a nut and freely rotates within the nut. The interlock reduces the number of parts necessary to be handled, eliminates the need for the nut to be of the same material as the ferrule, reduces the possibility of flow restriction or tubing deformation associated with rotation of the ferrule, and aids in the removal of the ferrule from the detail when removal is desired.

5 Claims, 2 Drawing Sheets

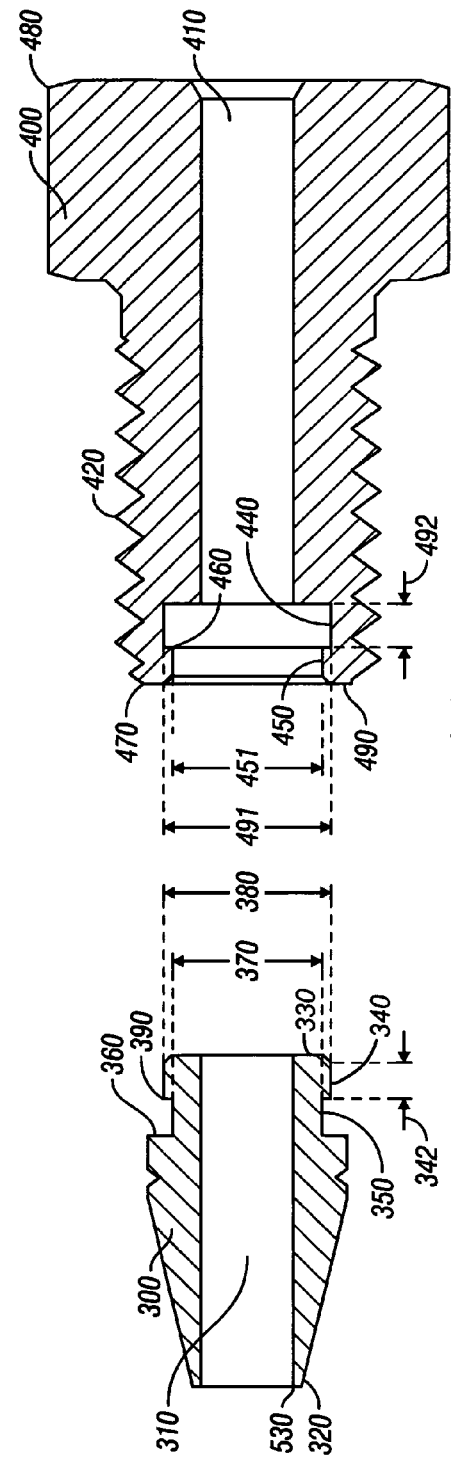

COMPRESSION FITTING NUT WITH INTERLOCKED FERRULE

CROSS-REFERENCE TO RELATED APPLICATIONS

This application claims the benefit of U.S. Provisional Patent Application No. 60/648,135 entitled, "Nut with Ferrule," filed on Jan. 28, 2005 in the United States Patent and Trademark Office.

STATEMENT REGARDING FEDERALLY SPONSORED RESEARCH OR DEVELOPMENT

Not Applicable.

FIELD OF INVENTION

This invention pertains to compression fittings for use in systems designed for chemical analysis.

BACKGROUND OF THE INVENTION

It is necessary in analytical systems to have fittings that create leak-tight seals. In such analytical systems, it is also desirous to have fittings which are inert relative to the sample components, which provide a flow path without inducing turbulence or mixing, and which adds minimal volume to the system.

Fitting designs which best address the aspect of added volume allow the tube ends which pass through such fittings to butt directly to each other or have bores which match the tubing bore, leaving no dead or unswept volume. Such fittings are called zero dead volume fittings. In analytical testing apparati dead volume is to be avoided as it reduces efficiencies of the test equipment, including gas columns.

Tubing used may be copper, stainless steel, or polymer based, including PEEK (Poly Ether Ether Ketone), PTFE (PolyTetraFluoroEthylene), ETFE (ethylene-tetrafluoroethylene), FEP (Flouridated Ethylene-Propylene), PFA (Perfluoroalkoxyethylene), and nylon.

One of the most common types of such zero dead volume fittings is a compression fitting. A zero dead volume compression fitting consists of a fitting body having a female fitting detail, tubing, a ferrule loosely riding on said tubing, and a male nut, also riding on said tubing. In operation the tubing is placed into the fitting body until the tubing end abutts the inner bore of the fitting body and seats correctly at the bottom of the fitting detail, the ferrule is then slid along the tubing until it engages the mating walls of the fitting body, and the nut is threadedly engaged so as to be retained in place and to fully press the ferrule against the mating wall of the fitting detail, causing the ferrule to apply pressure to the tubing and force such tubing against said bore of said fitting body.

A basic problem with such system is the number of parts, namely the fitting, the ferrule, the tubing and nut. Moreover such parts are typically small, permitting clasping by fingertips only. As can be anticipated and as is known in the prior art, as the tubing end is undeformed, the ferrule may slide off the tubing end after placement of the nut and the ferrule on the tubing but before insertion of the ferrule into the fitting body. Various manufacturers have attempted to reduce the number of parts, notably by molding a nut with a ferrule on its end. It is often desirable that equipment used for chemical analysis including the ferrule and nut be of an inert material so that the equipment does not react with the sample(s) being tested or the carrier(s) conveying the sample (s), which would contaminate the sample and produce false results. Selection of an inert material sufficient in strength to serve as the nut limits the number of materials available. Moreover as the molded ferrule contacts the fitting detail of the fitting body, tortional forces are created as friction between the molded ferrule portion and the fitting body opposes the force applied by the nut as it engages the fitting body threads. Such forces may weaken or destroy the assembly. An additional problem, distortion of the tubing, may also result from the use of such ferrule-nut assemblies. As the molded nut-ferrule assembly rotates, rotational forces are applied to the end of the tubing. Such forces may cause the tubing to twist relative to its opposition end or may result in deformation of the tubing end during rotation of the molded nut-ferrule assembly.

A further potential problem with the prior art nut and ferrule assembly may occur during removal of the prior art assembly from the fitting. During such assembly, the ferrule may resist removal from the fitting as a result of the forces applied during installation. As a result, the nut may be removed, leaving the ferrule still installed. Due to the size of the ferrule, removal from the detail in light of such installation forces can be difficult.

Therefore, it is a feature of the present invention to provide a nut and ferrule assembly which in operation reduces the number of loose parts, avoids the limitation of available materials, reduces the tortional problems associated with molded nut-ferrule assemblies, and reduces the potential for difficulties in disassembly.

SUMMARY OF THE INVENTION

The present invention pertains to a nut and ferrule assembly which reduces the number of parts necessary to be handled, eliminates the need for the nut to be of the same material as the ferrule, reduces the possibility of flow restriction or tubing deformation associated with rotation of the ferrule, and aids in the removal of the ferrule from the detail when removal is desired.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

In the drawings:

FIG. 2 is a cut-away side view of the instant invention.

FIG. 3 is a cut-away side view of the instant invention prior to assembly.

DESCRIPTION OF THE PREFERRED EMBODIMENT

Figure 1:
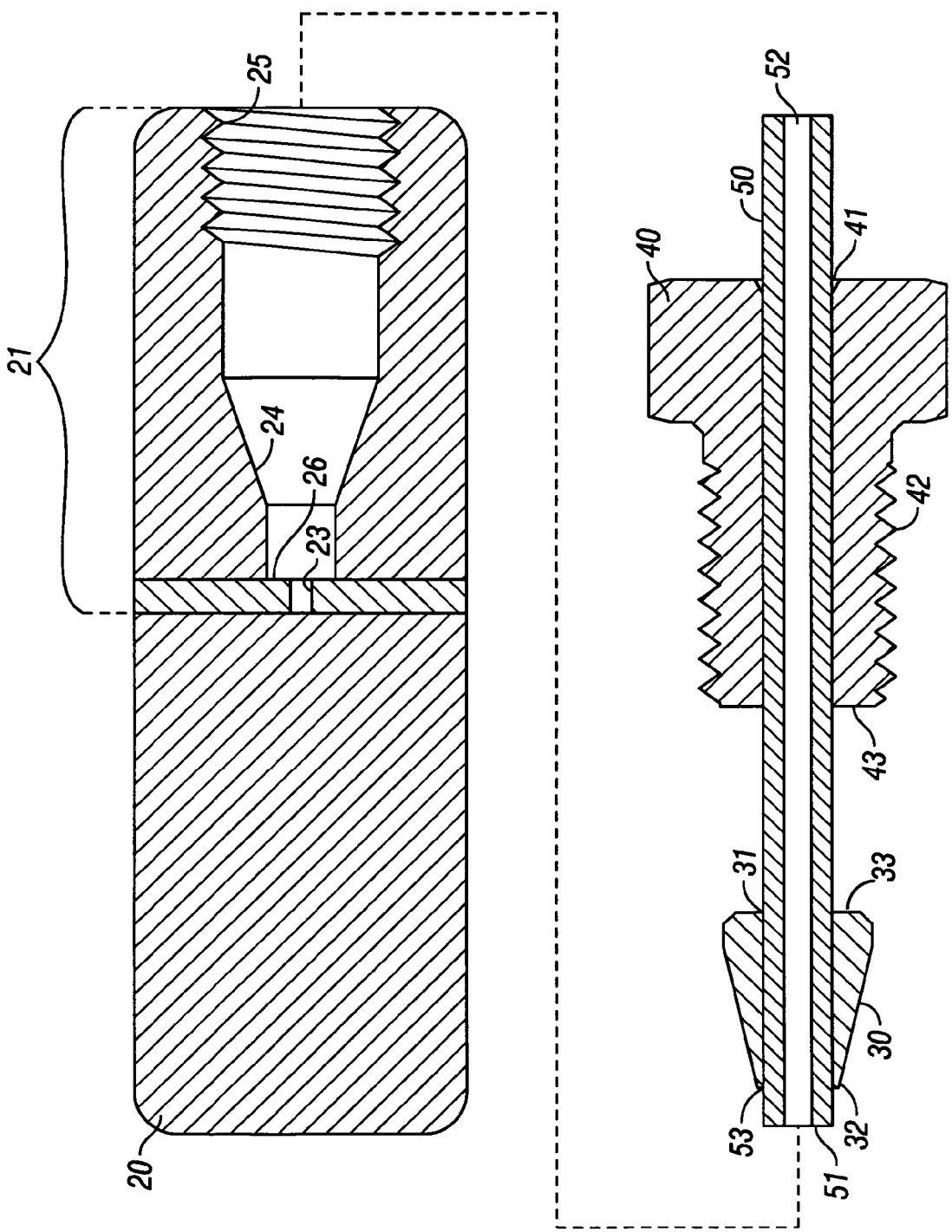
FIG. 1 is side view of a typical compression fitting with detail, tubing, nut and ferrule.

FIG. 1 depicts the prior art for a nut and ferrule assembly. Tubing 50 first passes through nut 40 at nut axial passageway 41 then through ferrule 30 at ferrule axial passageway 31, terminating in tubing end 51. Once assembled tubing end 51 abuts zero dead volume fitting detail bore bottom 26, aligning tubing 50 and tubing bore 52 with zero dead volume fitting detail bore 23. Nut 40 is then slid along tubing 50. Male threads 42 of nut 40 are then caused to engage female threads 25 of zero dead volume body fitting detail 21 which causes nut first end 43 to push ferrule 30 at ferrule second end 33. Ferrule 30 is wedge-shaped such that ferrule 30 contacts zero dead volume fitting detail ferrule seat 24. Typically an angle of 13 degrees from the axial centerline (26 degrees included) is used for the angled surface of ferrule 30 at ferrule first end 32. Typically an angle of 20 degrees from the axis centerline (40 degrees included) is used on fitting detail 21 to generate zero dead volume fitting detail ferrule seat 24. Alternatively ferrule 30 may be frustoconical. Upon application of force from nut 40 to ferrule 30, ferrule wedge end 32 is driven into female fitting detail 21 where ferrule first end 32 contacts zero dead volume fitting detail ferrule seat 24, creating inward hoop forces. Ferrule first end 32 is compressed about tubing 50 at tubing wedge impact 53 so as to retain tubing 50 in place as a result of the force exerted on ferrule 30 by nut 40.

Referring to FIG. 2, the instant invention, ferrule 300 interlocks freely-rotatably with nut 400. In the preferred embodiment ferrule 300 and nut 400 are composed of an inert material, through non-inert materials may also be used when desired. Referring to FIG. 3, like the prior art, ferrule 300 includes ferrule first end 320 and ferrule second end 330. Like the prior art, upon application of force from nut 400 to ferrule 300, ferrule 300 is driven into zero dead volume fitting detail 21 (not shown), retaining tubing 50 in abutment with zero dead volume fitting detail bore bottom 26 (not shown). Unlike the prior art, as ferrule 300 is interlocked with nut 400, it is not necessary to independently handle ferrule 300 or to attempt to align ferrule axial passageway 310 with tubing 50.

As shown in FIG. 3, ferrule 300 includes ferrule axial passageway 310, ferrule first end 320, ferrule second end 330, ferrule second end collar 340, ferrule second end neck 350, and ferrule load bearing shoulder 360.

To create and maintain interlock and free rotation between ferrule 300 and nut 400, it is important to maintain proper sizing of ferrule second end collar 340, ferrule second end neck 350, nut collar socket 440 and nut neck bore 450. Referring to FIG. 3, ferrule second end collar 340, i.e. ferrule second end collar diameter 380, is sufficiently greater in size than nut neck bore 450, i.e. nut neck diameter 451, to create a press-through fit when ferrule second end collar 340 mates to nut collar socket 440. Nut collar socket 440, i.e. nut collar socket diameter 491, is sufficiently greater in size than ferrule second end collar 340, i.e. ferrule second end collar diameter 380, that ferrule 300 and nut 400 freely rotate independently when ferrule second end collar 340 mates to nut collar socket 440. Ferrule second end neck 350, i.e. ferrule second end diameter 370 is sufficiently smaller in size than nut neck bore 450, i.e. nut neck diameter 451, that ferrule 300 and nut 400 freely rotate independently when ferrule collar 340 mates to nut collar socket 440. Likewise nut collar socket width 492 is sufficiently greater that ferrule second end collar width 342 that ferrule 300 and nut 400 freely rotate independently when ferrule second end collar 340 mates to nut collar socket 440.

It is likewise important to maintain proper sizing of the ferrule 300 and 400 as to effectively permit nut 400 to apply compressive forces to ferrule 300. In an alternative embodiment, ferrule 300 includes a ferrule load bearing shoulder 360, which permits loads to be transferred to ferrule 300 from nut load bearing face 490. In operation, ferrule first end 320 constricts first at tubing wedge impact 530 on tubing 50 (not shown) when forced into zero dead volume fitting detail ferrule seat 24 (not shown) when nut 400 bears against ferrule 300.

Beneficially, the interlock and free rotation of ferrule 300 and nut 400 permits ease of removal of ferrule 300 from zero dead volume fitting body 20 upon disassembly. During disassembly, as male threads 420 of nut 400 rotationally disengage female threads 25 of zero dead volume fitting detail 21, nut 400 is driven away from zero dead volume body 20. As nut 400 disengages, nut collar shoulder 460 engages ferrule collar shoulder 390 and draws ferrule 300 from zero dead volume fitting body 20. Ferrule 300 is thereby removed from zero dead volume fitting body 20 without difficulty.

It will be understood that while a preferred embodiment of the invention has been shown and described, the invention is not limited thereto. Many modifications may be made and will become apparent to those skilled in the art.

I claim:

1. A device for joining tubing to a zero dead volume fitting body for chromatography,
   said zero dead volume fitting body having a zero dead volume body fitting detail;
      said zero dead volume fitting detail having a zero dead volume fitting detail bore sized to receive said tubing;
      said zero dead volume fitting detail bore terminating at a zero dead volume fitting detail bore bottom;
      said zero dead volume fitting detail having a zero dead volume fitting detail ferrule seat;
      said zero dead volume fitting detail having female threads therein;
   said device comprising:
   a ferrule freely rotatably interlocked with a nut;
      said ferrule having a ferrule axial passage therethrough;
         said ferrule axial passage sized to permit said tubing to pass therethrough;
         said ferrule having a ferrule first end and a ferrule second end;
         said ferrule being wedge-shaped proximate said ferrule first end;
         said ferrule being radially compressible proximate said ferrule first end;
         said ferrule sized concentrically proximate said ferrule first end to constrict about said tubing upon compression;
            said ferrule second end having a ferrule second end neck;
            said ferrule second end neck having a ferrule neck diameter;
         said ferrule second end having a ferrule second end collar;
            said ferrule second end collar having a ferrule second end collar diameter;
               said ferrule second end collar diameter being greater than said ferrule second end neck diameter;
               and
      said nut having a nut axial passage therethrough;
         said nut axial passage sized to permit said tubing to pass therethrough;
         said nut having male threads;

said male threads of said nut being sized to be received by said female threads of said zero dead volume fitting detail;
said nut having a nut first end and a nut second end;
said nut first end having a nut collar socket;
said nut collar socket sized to receive said ferrule second end collar without interference;
said nut first end having a nut first end neck bore adjacent said nut collar socket;
said nut first end neck bore sized to receive said ferrule second end neck without interference;
said nut first end neck bore sized to permit passage of said ferrule second end collar by an interference fit.

2. The device of claim 1 wherein said ferrule is composed of a chemically inert material.

3. The device of claim 2 wherein said nut is composed of a chemically inert material.

4. The device of claim 2 said device further comprising:
a nut load bearing face at said nut first end; and
a ferrule load bearing shoulder;
said ferrule load bearing shoulder being located at the end of said ferrule second end neck proximate said ferrule second end.

5. A device for joining tubing to a zero dead volume fitting body for chromatography;
said zero dead volume fitting body having a zero dead volume body fitting detail;
said zero dead volume fitting detail having a zero dead volume fitting detail bore sized to receive said tubing;
said zero dead volume fitting detail bore terminating at a zero dead volume fitting detail bore bottom;
said zero dead volume fitting detail having a zero dead volume fitting detail ferrule seat;
said zero dead volume fitting detail having female threads therein;
said device comprising:
a ferrule freely rotatably interlocked with a nut;
said ferrule having a ferrule axial passage therethrough;
said ferrule axial passage sized to permit said tubing to pass therethrough;
said ferrule having a ferrule first end and a ferrule second end;
said ferrule being wedge-shaped proximate said ferrule first end;
said ferrule being radially compressible proximate said ferrule first end;
said ferrule sized concentrically proximate said ferrule first end to constrict about said tubing upon compression;
said ferrule second end having a ferrule second end neck;
said ferrule second end having a ferrule second end collar;
said nut; having a nut axial passage therethrough;
said nut axial passage sized to permit said tubing to pass therethrough;
said nut having male threads;
said male threads of said nut being sized to be received by said female threads of said zero dead volume fitting detail;
said nut having a nut first end and a nut second end;
said nut first end having a nut collar socket and a nut first end neck bore;
said nut first end neck bore being adjacent said nut collar socket;
said nut first end neck bore sized to permit passage of said ferrule second end collar by an interference fit.

* * * * *

UNITED STATES PATENT AND TRADEMARK OFFICE
CERTIFICATE OF CORRECTION

PATENT NO. : 7,316,777 B2  Page 1 of 1
APPLICATION NO. : 11/333944
DATED : January 8, 2008
INVENTOR(S) : H. Max Loy, Jr.

It is certified that error appears in the above-identified patent and that said Letters Patent is hereby corrected as shown below:

In Column 2, Lines 1-2, the phrase "sample (s)" should read --sample(s)--.
In Column 6, Line 19, the phrase "said nut; having" should read --said nut having--.

Signed and Sealed this

Sixth Day of May, 2008

JON W. DUDAS
*Director of the United States Patent and Trademark Office*